United States Patent [19]

Roggen

[11] Patent Number: 4,878,375
[45] Date of Patent: Nov. 7, 1989

[54] DEVICE FOR MEASURING HYDROGEN CONCENTRATION IN AN ALUMINUM MELT

[75] Inventor: Rolf Roggen, Sion, Switzerland

[73] Assignee: Swiss Aluminium Ltd., Chippis, Switzerland

[21] Appl. No.: 345,958

[22] Filed: May 1, 1989

[30] Foreign Application Priority Data

May 10, 1988 [CH] Switzerland .......................... 1774/88

[51] Int. Cl.[4] .............................................. G01N 7/10
[52] U.S. Cl. ........................................................ 73/19
[58] Field of Search ............................................ 73/19

[56] References Cited

U.S. PATENT DOCUMENTS

| | | | |
|---|---|---|---|
| 2,861,450 | 11/1958 | Ransley | 73/19 |
| 3,731,523 | 5/1973 | Vissers et al. | 73/19 |
| 4,056,968 | 11/1977 | Winslow, Jr. | 73/19 |
| 4,092,844 | 6/1978 | Oertle et al. | 73/19 X |
| 4,143,316 | 3/1979 | Roy et al. | 73/19 X |
| 4,181,005 | 1/1980 | Kanegae et al. | 73/19 |
| 4,454,748 | 6/1984 | Terai et al. | 73/19 |
| 4,624,128 | 11/1986 | Pelton | 73/19 |
| 4,757,707 | 7/1988 | Harvey et al. | 73/19 |

Primary Examiner—Michael J. Tokar
Assistant Examiner—Joseph W. Roskos
Attorney, Agent, or Firm—Bachman & LaPointe

[57] ABSTRACT

The device comprises an immersion probe (10) which is permeable to hydrogen and is made of melt-resistant sintered or calcined ceramic material connected, in a vacuum tight manner via a capillary tube (4), to a pressure gauge (2). The immersion probe (10) features at least two essentially plate-shaped diffusion membranes (7,8) that in each case form a common interface (9). The capillary tube (4) as such communicates freely with the interface (9). The immersion probe (10) is preferably situated in a crucible featuring openings above the level of the probe (10); on dipping the crucible into the melt 12, the openings allow the melt (12) to flow in, permit equalization of the hydrogen content of the metal and, after removing the crucible from the melt (12), allow the melt to flow out leaving a residual amount that protects the probe (10). The measuring probe is robust, easily changed and features a short response time.

15 Claims, 2 Drawing Sheets

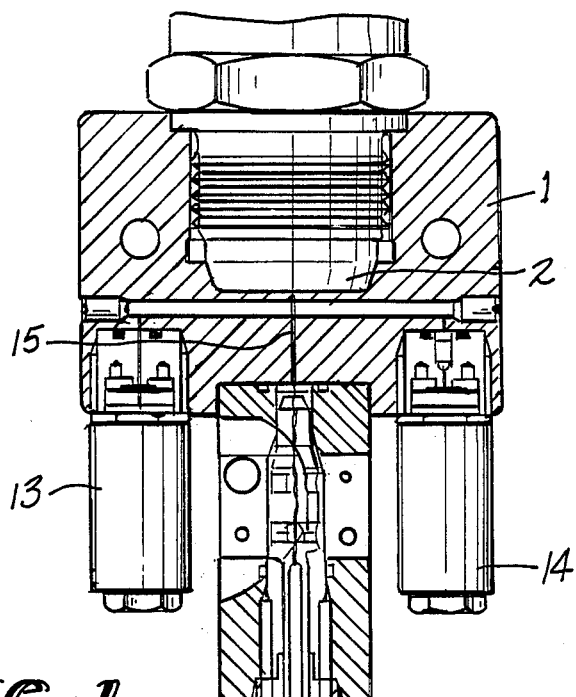
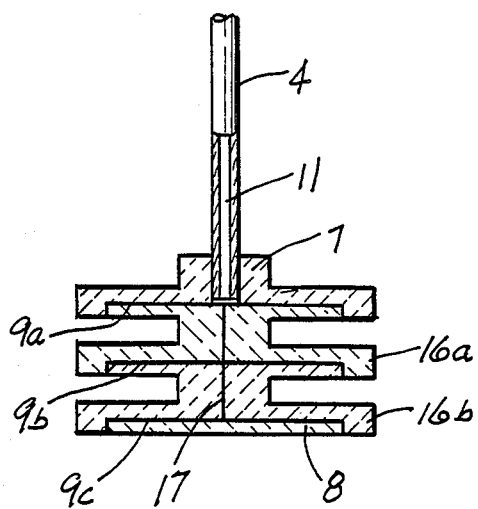
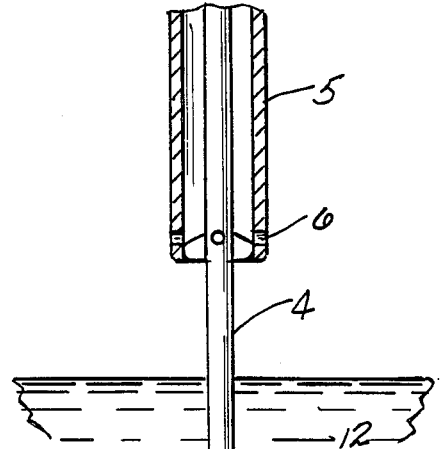
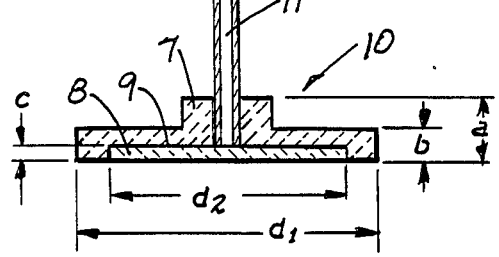
FIG-1
FIG-2

4,878,375

DEVICE FOR MEASURING HYDROGEN CONCENTRATION IN AN ALUMINUM MELT

BACKGROUND OF THE INVENTION

The invention relates to a device for measuring hydrogen concentration in an aluminum melt by means of an immersion probe that is permeable to hydrogen and is made of melt-resistant, sintered or baked ceramic material connected in a vacuum tight manner, via a fitting capilliary tube of melt-resistant material that is impermeable to hydrogen, to a pressure gauge situated in a measuring head. In aluminum and aluminum alloys the solubility of hydrogen differs greatly depending on the state and temperature of the metal. Aluminum melts readily take up hydrogen from furnace gases, humid air and furnace linings. With the addition of alloying elements such as Mg for example hydrides and hydrates are also taken up by the melt in addition to the dissolved hydrogen; these compounds increase the hydrogen content of the melt further. The solubility of hydrogen decreases drastically during solidification from about 0,8 to 0,04 $cm^3$ per 100 g of metal. The excess hydrogen precipitates out during solidification in the form of extremly fine pores which frequently diminish the mechanical properties of the finished product.

The demand for superior quality makes continuous supervision of the hydrogen content of the melt indispensible. Such supervision is usefully employed to check the metal quality just before the casting machine, to check the efficiency of melt treatment (degassing, removal of impurities with active gases) and to test insulating material for the release of hydrogen.

At present the methods for $H_2$-determination mentioned below are employed with various degrees of success. These methods make use of Sievert's Law which relates, under equilibrium conditions, the $H_2$ concentration of the melt to the $H_2$-partial pressure in a gas bubble and the melt temperature according to the following equation:

$$c = k_1 \sqrt{p} \cdot e^{-k_2/T}$$

where:
c = $H_2$ concentration in the melt ($cm^3$/100 g melt)
p = $H_2$ equilibrium pressure (mbar)
T = absolute temperature of the melt
$k_1$, $k_2$ = constants.

In one known process a circulating stream of nitrogen is introduced into the melt. When equilibrium saturation is reached, the hydrogen concentration is measured via a thermal conductivity cell. The high cost of the probes, which are susceptible to malfunctioning, and the need for trained personnel to operate them, limit the extent to which the instrument can be used in rough operating conditions.

Also known is to observe a melt sample in a transparent vacuum chamber under conditions of falling pressure. When the pressure becomes less than the equilibrium pressure of hydrogen in the melt, then bubbles form below the oxide skin. The instrument is robust enough for production conditions. The measurement, however, is subjective, and the method can not be employed with low $H_2$ concentrations ($\leq 0,10$ $cm^3$/100 g).

In another known hot-extraction method, samples that have been carefully prepared by machining are degassed in an inert gas stream either in the solid state at 500°–600° C. or after melting in vacuum. The process is labor intensive and therefore is expensive and can only be performed under laboratory conditions. The method is not suitable for magnesium-containing alloys because of getter effects and decomposition of hydride and hydrate.

In a further known method an immersion probe made of graphite and permeable to hydrogen but not the melt is dipped into the melt; the said probe is connected to a pressure measuring cell via a capillary tube. Impurity gases are first evacuated by means of a vacuum pump. The atomic hydrogen dissolved in the melt is recombined to hydrogen molecules on the graphite wall as in a gas bubble, and diffuses in the hollow body. The hydrogen content of the melt is then calculated via Sievert's Law from the equilibrium pressure of hydrogen and the melt temperature.

SUMMARY OF THE INVENTION

In view of these facts it is the object of the present invention to develop a device of the kind described hereinabove, the measuring probe of which is robust, easily exchanged and exhibits the shortest possible response time.

This object is achieved by way of the invention in accordance with the features of the present invention. The present invention comprises a device for measuring the concentration of hydrogen in an aluminum melt by means of an immersion probe that is permeable to hydrogen and is made of melt-resistant sintered or calcined ceramic material connected in a vacuum tight manner, via a fitting capillary tube of melt-resistant material that is impermeable to hydrogen, to a pressure gauge in a measuring head, in which, the immersion probe comprises at least two, essentially plate-shaped diffusion membranes that in each case form a common interface, and the capillary tube communicates freely with the interface/interfaces. Further preferred features of the invention are shown in the following specification.

BRIEF DESCRIPTION OF THE DRAWINGS

Further advantages and details of the invention are revealed in the following description of preferred exemplified embodiments of the invention; this with the aid of the drawing of a longitudinal cross-section viz., in FIG. 1 a device according to the invention with an immersion probe, FIG. 2 a further version of an immersion probe, and FIG. 3 an immersion probe protected by a crucible.

DETAILED DESCRIPTION

Figure 3:
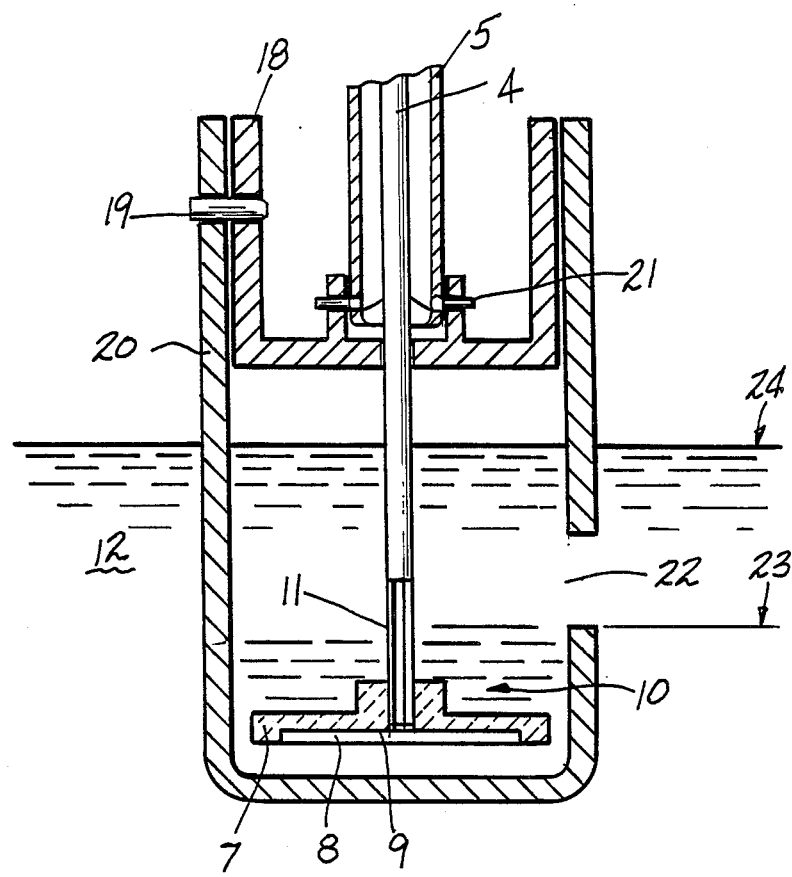

The device comprises essentially an immersion probe that is permeable to hydrogen and impermeable to the melt, a capilliary tube with integral thermocouple, a protective sleeve and a push-fit connection. The shape of the immersion probe provides the largest possible exchange surface with the melt stream at the smallest possible gas volume in contact with the pressure gauge. The dimensions of the probe correspond approximately to half of the width of the channel in the trough systems normally employed in cast houses.

The immersion probe, which is permeable to hydrogen, is at least in two parts. The uppermost part (diffusion membrane) is connected via the capilliary tube to the pressure gauge via the measuring head. The lower part (diffusion membrane) is in the simplest case disc-shaped and lies, close-fitting, in the upper part. The seal at the place of joining of the two parts and at the joint between the upper part and the capilliary tube is made by the melt. The immersion probe is made of a heat-resistant material that does not react with the melt. The porosity of the membrane is sufficient to allow a $H_2$-exchange melt/capillary tube without penetration of the melt. Sintered or calcined materials, that are not wet by the melt, can be used by way of preference e.g. graphite, boron nitride, silicon nitride, alumina or aluminum oxide. etc.

The capillary tube is made of a material that is permeable to hydrogen but does not react with the melt. High density alumina or aluminum oxide tubes can be used by way of preference. Metallic capillary tubes with protective coatings such as e.g. steel or nickel tubes plasma-coated with $Al_2O_3$ can also be employed. The outer diameter should be kept as small as possible in order to minimize the flow of heat to the holding device. Further, on immersing the probe, the oxide skin on the melt that is dragged-in can produce unsealed places on the surface of the tube. These non-sealed regions are proportional to the diameter of the pipe and in the case of large diameters would falsify the measurement. The thermocouple is preferably a Ni-Cr sheathed element that projects, sheathed by the capillary tube, into the immersion probe.

The connection of the probe to the measuring head is made via a connecting member. As such the capillary connection and the electrical connections are in the form of vacuum-tight plugs or screw-type connections. The overall volume of the gas column (dead space in the measuring instrument) should be smaller than 1 $cm^3$ in order to ensure a response time of a few minutes. The hydrogen which is uniformly distributed in the melt or enriched on the surface of entrained oxide particles, precipitates on the surface of the immersion probe. This process takes place in various reversible steps:

(1) By convection or pouring, fresh melt flows past the immersion probe. The hydrogen is mainly in solution (as proton and free electron).

(2) Change of state in which hydrogen changes from the dissolved state to adsorption of the atom on the surface of the probe.

(3) Desorption and recombination of the atoms to $H_2$ molecules.

(4) Diffusion through the permeable probe.

(5) Accumulation and increase in pressure of the previously carefully evacuated probe. The gas flows through the contact surface of the, at least, two piece probe via the capillary tube and push-fit connection to the measuring instrument. Under equilibrium conditions the pressure of hydrogen in the probe is a function (Sievert's Law) of the $H_2$ content of the melt and its temperature. The response time of the probe is given by the ratio of the rate of diffusion to the dead space in the probe.

In order to be able to perform the measurement with a large dead space in an acceptable time, a hydrogen feed facility can be provided in the measuring head in addition to the evacuation valve. According to the change in pressure therefore $H_2$ can be quickly supplied to or removed from the measuring head in given amounts by means of a PID control regulated by a process control computer.

The almost simultaneous determination of pressure and temperature at the same place in the melt being investigated ensures accurate determination of the hydrogen content of the melt. The simple external shape of the probe makes it easier, when the probe is to be reused, to remove any adherent hydroxide which under some circumstances can give the impression of the hydrogen content being greater than it actually is. The device permits quick, safe exchange of probes in the rough surroundings and conditions of the cast house. The arrangement ensures long-term operation of the probe without erroneous measurement.

A device for measuring the concentration of hydrogen in an aluminum melt features, as shown in FIG. 1, a measuring head 1, a pressure gauge 2 with membrane flush at the front. The measuring head 1 is connected in a vacuum-tight manner via a quick-fit connection 3 to a capillary tube 4 of high density alumina which has an outer diameter of, for example, 4 mm. The capillary tube 4 is surrounded by a protective sleeve 5 which is cooled by compressed air, and is supported at its lower end featuring outlet holes 6. The free end of the capillary tube fits into a bell-shaped first diffusion membrane 7 made of graphite, into which a second disc-shaped diffusion membrane 8 fits forming a common interface 9. The diffusion membrane 7,8 as such form the immersion probe 10. Typical dimensions of the probe 10 as shown in FIG. 1, are a=10 mm; b=5 mm; c=2 mm; d=50 mm; $d_2$=40 mm. Within the capillary tube 4 and fitting flush with it is a Ni-Cr thermocouple 11 having a diameter of, for example, 1,5 mm. The thermocouple 11, sheathed by the capillary tube 4, projects into the first diffusion membrane 7. The capillary tube 4 with immersion probe 10 mounted on it is shown dipping into an aluminum melt 12.

Connecting up with the measuring head 1 are a vacuum valve 13 and a hydrogen feed valve 14. pressure gauge 2, vacuum valve 13, hydrogen feed valve 14 and capillary tube 4 are all interconnected via connecting channel 15.

FIG. 2 shows in some detail the construction of another version of the immersion probe 10. In that case the diffusion membranes are stacked as cells with two intermediate parts 16a,b inserted between the first and the last membranes 7,8. The interfaces 9a,b,c are interconnected via a bore 17 acting as hydrogen collection channel, and connect up with the capillary tube 4. The exchange surface in contact with the melt can be made as large as desired without significantly increasing the dead space; this by the selection of the appropriate number of intermediate parts 16.

FIG. 3 shows a version of the lower part of the device shown in FIG. 1. The probe 10 is situated in a crucible 20 e.g. of aluminum oxide immersed in the melt 12. In the lower region, above the probe 10, the crucible 20 features at least one opening 22 which is of relatively large diameter. Usefully there are three such openings in the crucible wall situated at radial points 120° C. from each other. The crucible 20 is suspended from a beaker-shaped holder 18 e.g. of heat-resistant steel releasably attached to the protective sleeve 5. The attachment is made by generally known mechanical means such as screws 19,21, bolts, pins, outer and inner threads, or bayonet type fittings.

On dipping the crucible 20 into the melt 12, the melt 12 flows through the openings 22 into the crucible interior and reaches a first level 24 corresponding to the melt surface outside the crucible 20. The hydrogen content of the melt 12 equalizes itself via the completely open openings 22. After taking the measurement, the device is raised out of the melt. On doing so the crucible is partly emptied via the openings 22, i.e. down to a lower second level 23 given by the position of the openings 22. The probe 10 is always protected in an air-tight manner by the melt remaining in the crucible 20. While the device is not in service, it can be placed up to the height of the crucible in a vertical holding furnace and is at all times ready for the next measurement.

This version of crucible is particularly advantageous as the immersion time can be again reduced and a lifetime of several months achieved. Furthermore, one can prevent hydroxide phases forming on the surface of the probe 10 i.e. phases that form on adherent aluminum cooled in contact with air and release gas in the melt falsifying the result of measured $H_2$ content.

I claim:

1. Device for measuring the concentration of hydrogen in an aluminum melt which comprises: a measuring head; a pressure gauge associated with said measuring head; a capillary tube of melt-resistant material that is impermeable to hydrogen connected to said pressure gauge; and an immersion probe that is permeable to hydrogen and is made of melt-resistant ceramic material connected to said capillary tube, wherein the immersion probe comprises at least two, essentially plate-shaped diffusion membranes that in each case form a common interface, and wherein the capillary tube communicates freely with said interface.

2. Device according to claim 1 wherein said immersion probe is made of sintered ceramic material.

3. Device according to claim 2 wherein said immersion probe is made of calcined ceramic material.

4. Device according to claim 1 wherein the first diffusion membrane accommodates the capillary tube and features a recess into which the second diffusion membrane fits.

5. Device according to claim 4 wherein said immersion probe is a multi-part probe provided with at least one intermediate part, one side of which in each case features a recess to accommodate the next intermediate part, wherein the interfaces are interconnected via a bore and to the capillary tube.

6. Device according to claim 1 including a thermocouple provided in the capillary tube at the end facing the immersion probe.

7. Device according to claim 5 wherein the thermocouple fits flush with the capillary tube.

8. Device according to claim 1 including a crucible suspended from the measuring head, wherein the immersion probe is arranged in said crucible, said crucible including at least one opening above the immersion probe at the side thereof.

9. Device according to claim 7 including a protective sleeve on said capillary tube for protecting the capillary tube and attached to the measuring head, wherein said crucible is suspended from said sleeve.

10. Device according to claim 9 wherein said crucible is suspended from said sleeve from a beaker-shaped holder.

11. Device according to claim 1 wherein the dead space of the measuring instrument corresponding to the total volume of the case column, is smaller than 1 $cm^2$.

12. Device according to claim 1 wherein the measuring head includes a vacuum valve and a hydrogen feed valve and is able to supply hydrogen to the measuring probe.

13. Device according to claim 1 wherein the measuring head includes a vacuum valve and a hydrogen feed valve and is able to remove hydrogen from the measuring probe.

14. Device according to claim 7 wherein the immersion probe and the crucible are made of a material selected from the group consisting of graphite, boron nitride, silicon nitride and aluminum oxide.

15. Device according to claim 1 wherein the capillary tube is made of high density aluminum oxide.

* * * * *

UNITED STATES PATENT AND TRADEMARK OFFICE
CERTIFICATE OF CORRECTION

PATENT NO. : 4,878,375
DATED : November 7, 1989
INVENTOR(S) : ROLF ROGGEN

It is certified that error appears in the above-identified patent and that said Letters Patent is hereby corrected as shown below:

In Column 6, claim 7, line 6, "claim 5" should read --claim 6--.

In Column 6, claim 9, line 13, "claim 7" should read --claim 8--.

In Column 6, claim 14, line 31, "claim 7" should read --claim 8--.

Signed and Sealed this

Sixteenth Day of October, 1990

Attest:

HARRY F. MANBECK, JR.

*Attesting Officer*  *Commissioner of Patents and Trademarks*